United States Patent [19]

Choy-Maldonado

[11] Patent Number: 5,613,262

[45] Date of Patent: Mar. 25, 1997

[54] LINGUAL BRUSH

[76] Inventor: Gina N. Choy-Maldonado, 24 Calle 0-63, Zona 1, Guatemala City 01001, Guatemala

[21] Appl. No.: 280,678

[22] Filed: Jul. 27, 1994

[51] Int. Cl.$^6$ ............................. A46B 9/02; A46B 9/06
[52] U.S. Cl. .................... 15/160; 15/143.1; 15/167.1; 15/207.2; 15/DIG. 6; 606/161; D4/104
[58] Field of Search .................... 15/143.1, 160, 15/167.1, 207.2, DIG. 6; 606/161; D4/104, 134

[56] References Cited

U.S. PATENT DOCUMENTS

| | | | |
|---|---|---|---|
| 306,776 | 10/1884 | Rhein | 15/167.1 |
| D. 309,528 | 7/1990 | Valenti | D4/134 |
| 914,501 | 3/1909 | McEachern | 15/167.1 |
| 1,891,864 | 12/1932 | Barrett | 606/161 |
| 2,064,860 | 12/1936 | Sekine | 15/167.1 |
| 3,072,944 | 1/1953 | Clayton et al. | 15/167.1 |
| 3,943,592 | 3/1976 | Bhaskar et al. | 15/160 |
| 4,274,174 | 6/1981 | Ertel | 15/143.1 |
| 4,538,631 | 9/1985 | Prince | 15/167.1 |
| 4,638,521 | 1/1987 | Potente et al. | 15/167.1 |
| 4,672,706 | 6/1987 | Hill | 15/143.1 |
| 4,679,273 | 7/1987 | Okin | 15/167.1 |
| 4,706,322 | 11/1987 | Nicolas | 15/167.1 |
| 4,724,570 | 2/1988 | Hitzman | 15/143.1 |
| 4,729,142 | 3/1988 | Yoshioka | 15/167.1 |
| 4,738,001 | 4/1988 | Shipp | 15/167.1 |
| 4,882,803 | 11/1989 | Rogers et al. | 15/167.1 |
| 5,226,197 | 7/1993 | Nack et al. | 15/160 |
| 5,305,489 | 4/1994 | Lage | 15/207.2 |

FOREIGN PATENT DOCUMENTS

| | | | |
|---|---|---|---|
| 557790 | 8/1923 | France | 15/167.1 |
| 2232284 | 1/1975 | France | 15/167.1 |
| 3129645 | 3/1983 | Germany | 15/167.1 |
| 5-168528 | 7/1993 | Japan | 15/167.1 |
| 16790 | of 1897 | United Kingdom | 15/160 |
| 438858 | 11/1935 | United Kingdom | 15/167.1 |
| 91-19437 | 12/1991 | WIPO | 15/167.1 |

*Primary Examiner*—Mark Spisich
*Attorney, Agent, or Firm*—John S. Hale; Gipple & Hale

[57] ABSTRACT

A device for cleaning the surface of the tongue comprising an elongated handle having a brushhead attached to one end thereof which extends from the brush head at an angle of at least 15°. The brush head has a flat surface with a plurality of bristle cells extending therefrom at least 4–6 mm with the opposite side of the brush head being rounded.

13 Claims, 6 Drawing Sheets

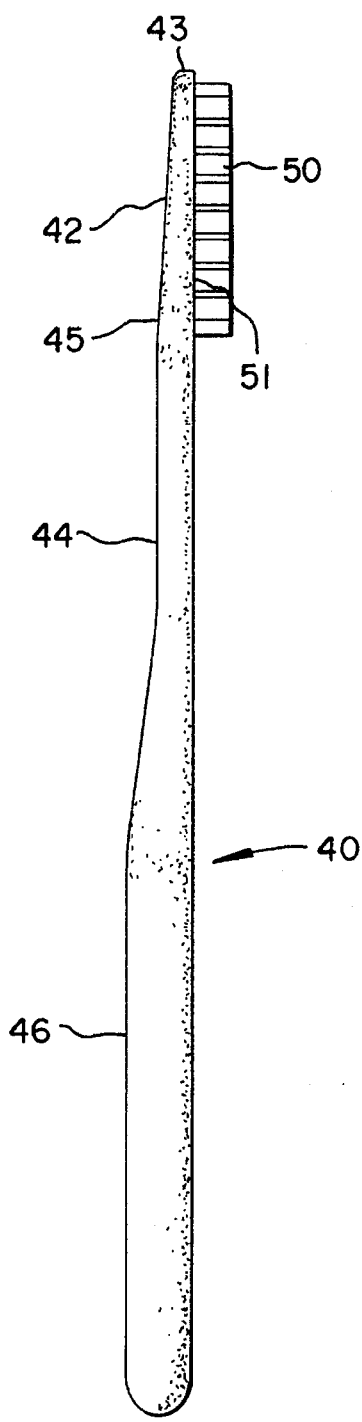
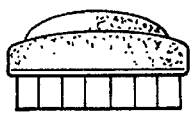
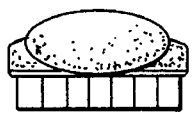
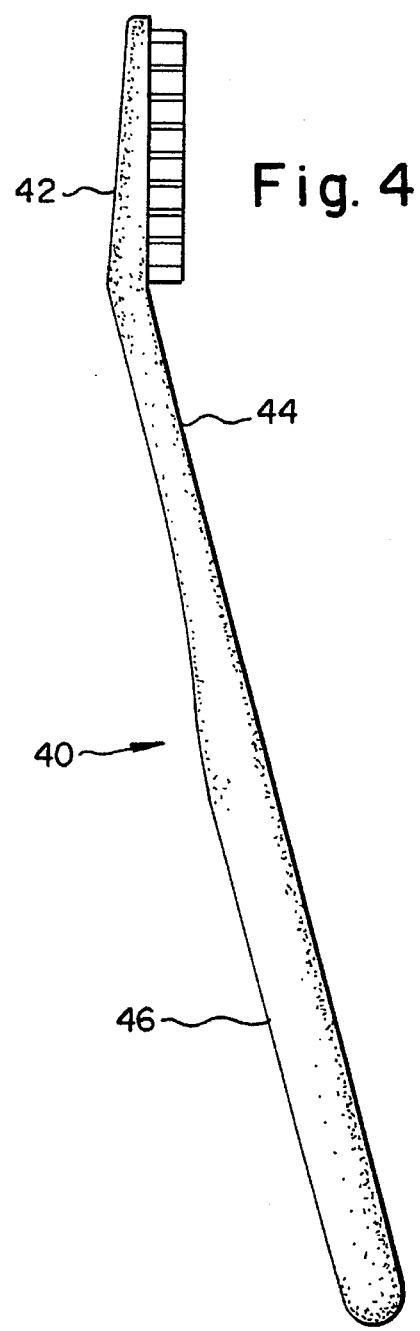
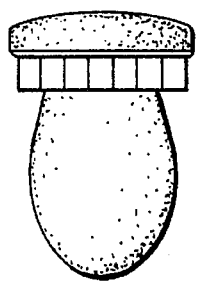
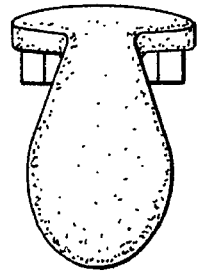

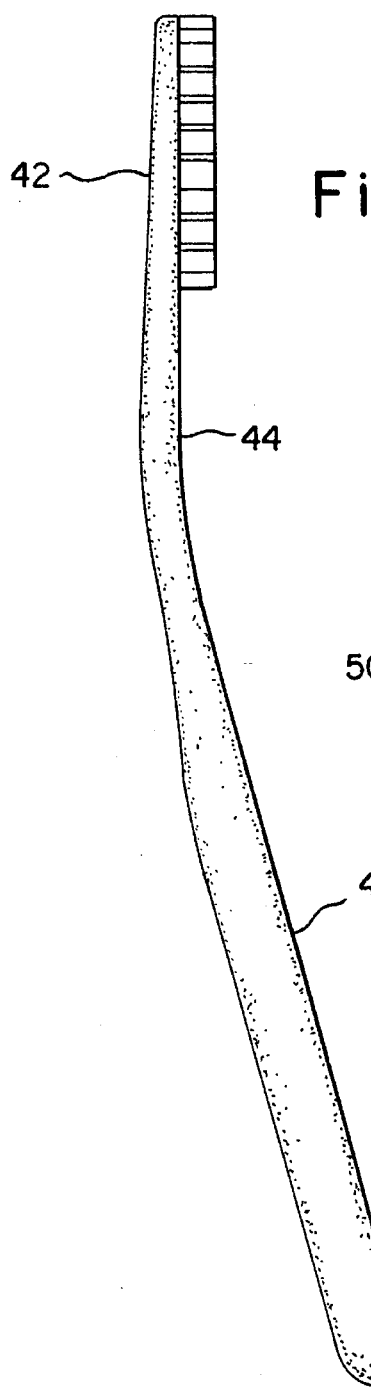
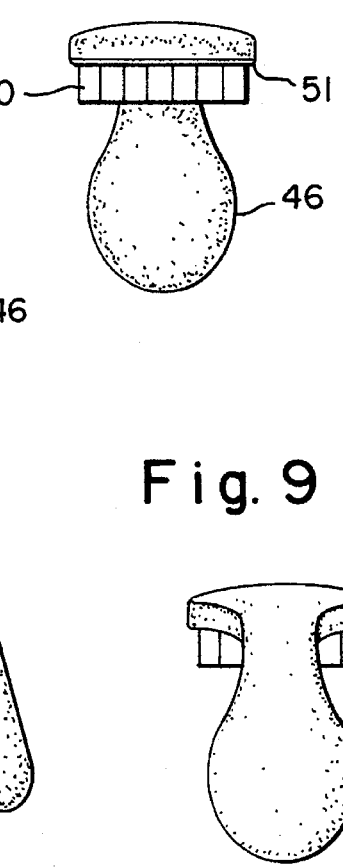
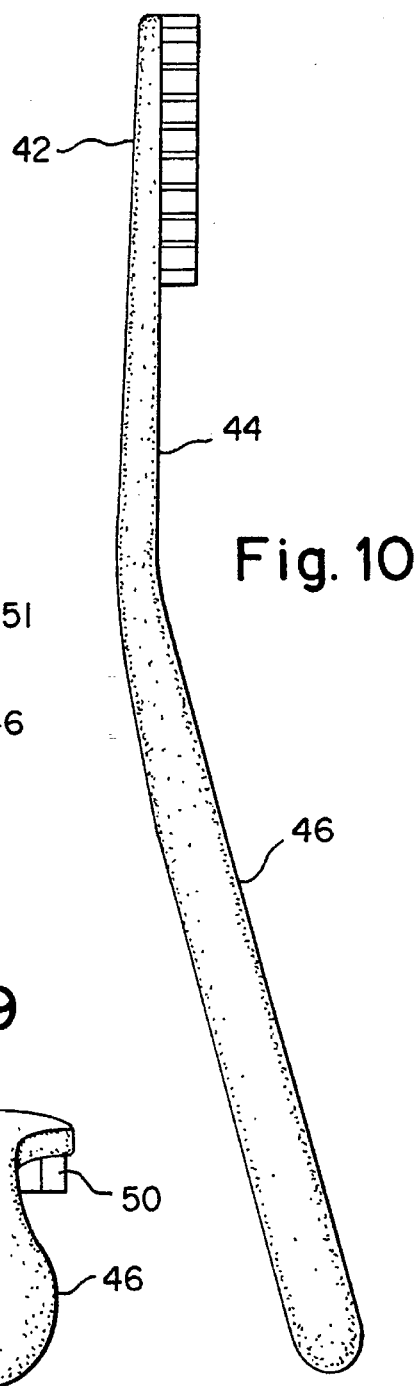
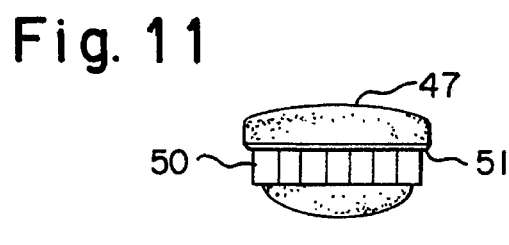
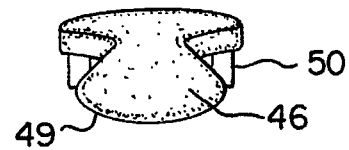

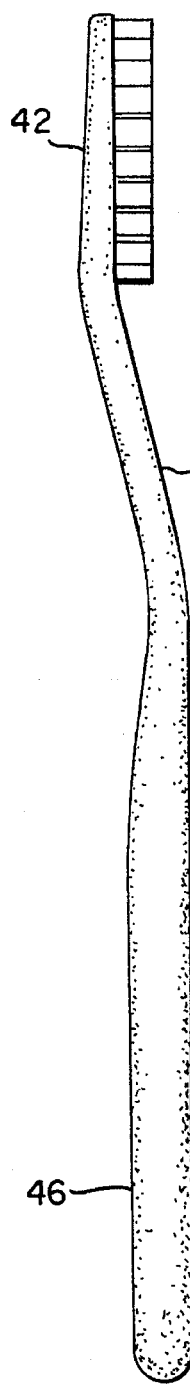
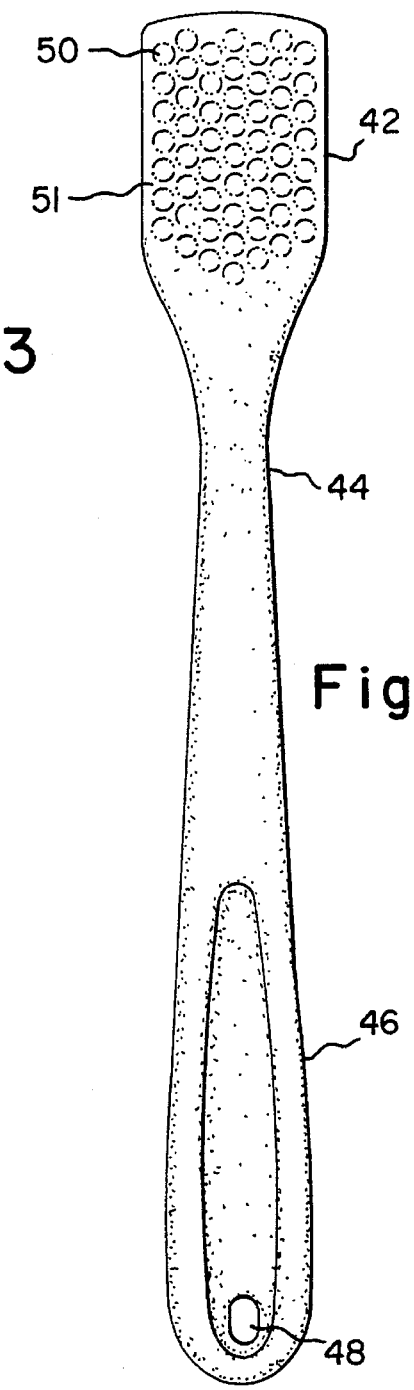
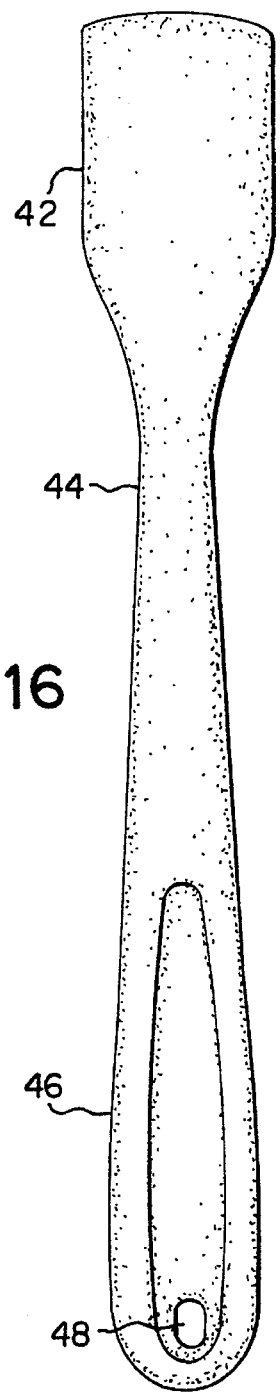
Fig. 13
Fig. 16
Fig. 17
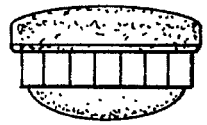
Fig. 14
Fig. 15

LINGUAL BRUSH

I. BACKGROUND OF THE INVENTION

The present invention is generally directed towards a brush device and more specifically is directed towards a lingual brush with an oriented bristle assembly and angled handle.

The lingual brush is important in the cleaning of the tongue. The tongue is a muscular and mobile organ which performs a number of functions such as:

1. The tasting or differentiation of flavors.
2. Moves the food towards the teeth to be chewed.
3. Provides for the deglution of food; and
4. Allows the articulation of words.

The tongue in the oral cavity is the principal habitant of microorganisms like bacteria, viruses and particles coming from the external environment, as it is directly exposed to the external environment when the mouth is opened. The tongue is also exposed to the microorganisms that come in foods with the consequent growth (development) of aerobic and anaerobic bacteria when the mouth has been closed for a long period of time as during a period of sleep.

The tongue is a muscular organ having a different cover from all other covers of the body that are in direct contact with the ambient atmosphere. The mucous membrane that covers the dorsal surface of the tongue is the perfect habitat for microorganisms that produce serious illnesses.

The body of the tongue comprises two-thirds of the tongue's length and lies horizontally in the oral cavity. Further back, near the throat, comprising one-third of its length, is the root or base of the tongue. The body of the tongue carries the lingual papillae, while the base of the tongue is covered with tonisllar tissue.

The top surface of the tongue is covered with mucosa membrane. This mucosa is characterized by the presence of numerous lingual papillae, some of which have a mechanical function (the tongue assists in the process of chewing), while others carry the specialized taste organs or taste buds.

The lingual papillae consist of large, specialized connective tissue papillae, covered with orthokeratinized stratified squamous epithelium.

The basic structure of a (specialized) connective tissue papilla is that of a conical mound (or a ridge, in the case of foliate papillae) which constitutes primary papilla. On top of the primary papilla several smaller conical peaks or ridges are present. These are the secondary papillae.

There are four types of lingual papillae namely; filiform papillae, fungiform papillae, vallate papillae, and foliate papillae.

Filiform Papillae.

These are the most abundantly present lingual papillae. They are distributed over the entire surface of the body of the tongue and are covered with a thick layer of keratinized epithelium. These papillae have a purely mechanical function, and they are the only papillae without taste buds.

Fungiform Papillae.

These papillae are far less numerous than the filiform papillae. They are distributed among the filiform papillae and show as reddish dots on the surface of the tongue. They are shaped somewhat like mushrooms. A thin, keratinized epithelium covers their surfaces. The thinness of the epithelium allows the red of the blood vessels in the connective tissue papilla to show through. This condition is responsible for the red color of these papillae. On its top surface a fungiform papilla may carry one or several taste buds.

Vallate Papillae.

These large papillae are located in a V-shaped groove at the border between the body and base of the tongue. There are only 8 to 12 of these papillae. Their shape resembles that of the fungiform papillae, but the vallate papillae are sunk somewhat below the surface of the tongue, so that they are surrounded by a groove and a low, circular wall of oral mucosa. These papillae are covered with keratinized epithelium. Several taste buds are present on the vertical (side) surface of the papilla, facing the surrounding groove.

Foliate Papillae.

These papillae are found in 4 to 11 ridges, running parallel with each other on the side of the tongue, near the tongue base and may not easily be visible clinically. They are covered with keratinized epithelium and carry several taste buds on their sides.

The deepest part of the grooves surrounding the vallate papillae and the grooves between adjacent foliate papillae contain the openings of ducts of special salivary glands, the von Ebner glands. The saliva from the glands rinses the grooves continuously to enable the taste buds to perceive several different taste stimuli in sequence.

The lingual surface thus presents, numerous small conical and mushrooms shapes, and it facilitates the accumulation of suburral material which is principally composed of food residues and bacteria. On clinical examination the suburral material can be seen as a white coat that obstructs a clean surface and the natural red color.

In addition to the above noted functions a physician can obtain significant medical information from the tongue upon observing the lingual surface so that one can detect illnesses such as scarlet fever and pernicious anemia due to specific alterations in this region, caused by pathological entities. Current statistics also register an increase in the number of oral carcinoma cases.

The registered frequency in lingual pathology cases on which the tongue furrows and/or crypts containing deposited food residues, generally show lesions present as growth in the papillae, with sizes up to 3, 6, and/or 9 mm producing inflammation. The symptoms give a burning sensation and pain that generally decreases when the principal cause agent is eliminated A remarkable improvement in the lesions is obtained by removal of an excessive accumulation of the suburral pigmented coat.

The etiology of the different illnesses of the tongue has been attributed: poor oral hygiene, the habit of smoking, the use of antibiotics, exposure to radiations (hospital patients), and to systemic factors.

Furthermore the suburral material is the principal cause of the poor oral breath and hinders the function of the tongue as a sensual organ.

Therefore it is of great importance to do a correct and adequate cleaning of the tongue with a specific instrument called a lingual brush. Such an instrument allows the removal the greatest possible quantity of suburral material, the remainder being removed away through the natural self-cleaning mechanism, which in the case of the tongue, is carried out by the vallate papillae which only exist in a limited number.

Unfortunately the population does not engage in daily tongue hygiene due principally to the fact that a specific instrument for conducting this hygiene is not available. Only an almost nonexistent minority of the population carries out this practice, primarily by employing a regular toothbrush that, as its name suggests, has been designed for the teeth that have hard surfaces and are structurally different to the lingual organ.

Several patents have been directed towards lingual brushes and an attempt to provide instruments which can be used by the general public. A pertinent prior art lingual hygiene brush is shown in Guatemalan Patent Number MU-89001 in which a flat headed rectangular shaped brush head is mounted on a rounded oblong handle which extends at a 15° angle from the horizontal axis of the brush head. The handle defines an aperture at one end allowing the lingual brush to be hung from a hook or a support and the brush head is provided with a plurality of bristles aligned in rows along the brush head. Another lingual brush is shown in U.S. Pat. No. 5,226,197 in which a flat brush body is formed with an elongated handle having a rounded end. The handle has a decreased width in the neck area leading to a brush head provided with rows of short bristles. A semi-rigid scrapper component is provided on the front edge of the distal end of the brush head. The bristles are triangularly shaped with each bristle having a larger head decreasing in size as it extends down to the stem of the bristle which is embedded in the plastic material of the head. A combined toothbrush, tongue scraper and ear cleaner device is shown in U.S. Pat. No. 3,254,356. In this patent a flat brush body is provided at one end with a elongated rectangular head having a plurality of bristles secured thereto in rows while the handle end is provided with a ball-like knob which is semi-spherical for use in cleaning an ear canal. The handle portion is flexible allowing the body to bend. U.S. Pat. No. 4,079,478 shows a tongue brush with a flat head and a handle that angles outward into a pistol type grip. The brush is provided with a removable fibrous cleaning member which can be slidably mounted in the brush head allowing the fibrous material to then be rubbed back and forth against the tongue. Another tongue cleaning device is shown in U.S. Pat. No. 3,943,592 in which a flat tongue depressor type body is coated at one end with a base fabric having flexible hooks which are commonly referred to under the trademark VELCO® type hooks.

U.S. Pat. No. 2,651,068 and 2,574,654 disclose tongue cleaners having a tooth brush type head and bristle assembly mounted on one end the body and a scrapper structure mounted on the other end of the brush handle. U.S. Pat. No. 2,583,750; 2,543,999; 2,491,274; and 697,336 are directed to tongue scrapers provided respectively with scrapping ridges, sharp scrapping edges, U-shaped body having an upper surface with a knife edge and a lower face provided with bristles, and a single piece of synthetic foam sponge material.

II. SUMMARY OF THE INVENTION

The tongue surface accumulates residues and microorganisms forming a suburral coat that must be removed away from the mouth. Accordingly, it is an object of the present invention to provide a lingual brush which can remove food, debris from the grooves, and clean the papillae on the dorsal surface of the tongue. The present lingual brush is provided with a brush head provided with bristle sets in specific geometric orientation extending 4 to 6 mm from the brush head face and an angled handle extending from the axis of the brush head.

It is an object of the invention to provide an instrument, that posesses the qualities of wiping the tongue's suburra, while being designed in a functional and anatomic way for such purpose.

It is another object of the invention to provide a tongue cleaner which is thin enough in design to preclude a gag reflex which precludes proper cleansing of the tongue.

It is yet another object of the invention to provide a tongue cleaner with no sharp edges which can damage tissues in the oral cavity during the cleaning process.

Another object of the invention is to provide a tongue cleaner which is simple to manufacture inexpensively to allow general availability to the general public for use as part of their oral hygiene.

In the accompanying drawings, there is shown an illustrative embodiment of the invention from which these and other of objectives, novel features and advantages will be readily apparent.

III. BRIEF DESCRIPTION OF THE DRAWINGS

FIG. 1 is a side elevation view of the lingual brush;

FIG. 2 is a front elevation view of the lingual brush shown in FIG. 1;

FIG. 3 is a rear elevation view of the lingual brush shown in FIG. 1;

FIG. 4 is a side elevation view of another embodiment of the lingual brush;

FIG. 5 is a front elevation view of the lingual brush shown in FIG. 4;

FIG. 6 is a rear elevation view of the lingual brush shown in FIG. 4;

FIG. 7 is a side elevation view of yet another embodiment of the lingual brush;

FIG. 8 is a front elevation view of the lingual brush shown in FIG. 7;

FIG. 9 is a rear elevation view of the lingual brush shown in FIG. 7;

FIG. 10 is a side elevation view of still another embodiment of the lingual brush;

FIG. 11 is a front elevation view of the lingual brush shown in FIG. 10;

FIG. 12 is a rear elevation view of the lingual brush shown in FIG. 10;

FIG. 13 is a side elevation view of another embodiment of the lingual brush;

FIG. 14 is a front elevation view of the lingual brush shown in FIG. 13;

FIG. 15 is a rear elevation view of the lingual brush shown in FIG. 13;

FIG. 16 is a top plan view of the lingual brushes shown in FIGS. 1, 4, 7, 10 and 13;

FIG. 17 is a bottom plan view of the lingual brushes shown in FIGS. 1, 4, 7, 10 and 13;

IV. DETAILED DESCRIPTION OF THE INVENTION

Figure 18:
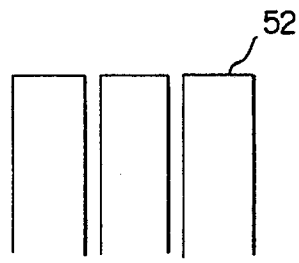
FIG. 18 is an enlarged cross section of flat ended bristle members which can be used with the lingual brush.
Figure 19:
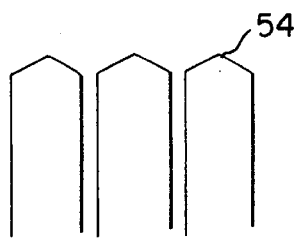
FIG. 19 is an enlarged cross section of angle or peak ended bristle members which can be used with the lingual brush.
Figure 20:
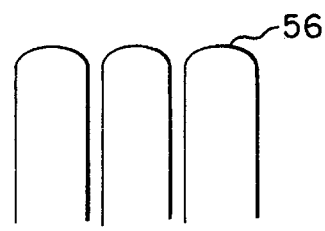
FIG. 20 is an enlarged cross section of rounded ended bristle members which can be used with the lingual brush.
Figure 21:
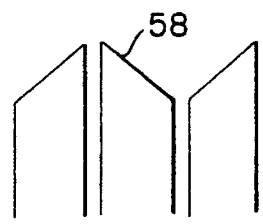
FIG. 21 is an enlarged cross section of inclined ended bristle members which can be used with the lingual brush.

The preferred embodiment and best mode of the invention is shown in FIGS. 10–12, 16, 17 and 26.

The present invention comprises a lingual brush 40 which is of single piece molded plastic construction constructed of a head 42, a neck 44 and a handle 46. The preferred embodiment has a square or rectangular bristle head 42 with a length ranging from 2.5 cm to 3.5 cm and a width ranging from 1.5 cm to 2.5 cm. The head is preferably tapered with the distal end being of lesser thickness than the proximal portion of the head. The sides of the head are rounded. The head brush bristle face surface is flat and the opposite brush head surface is rounded to prevent tissue tearing or bruising.

The neck 44 has a length ranging from 3.5 cm to 4.0 cm and a width ranging of 0.80 cm to 1.0 cm. The neck extends from the head and forms an angle close to the handle of 15° for large and medium sizes and 10° for the small size. This angle facilitates the handle of the brush with respect to the position and anatomy of the tongue. The handle 46 has a length ranging from 9.0 cm to 11.5 cm and a width ranging from 1.5 cm to 2.5 cm. The overall length of the brush ranges from 15 cm to 19 cm depending upon the size used.

The lingual brush 40 is made of synthetic polymers as for example polyprophylene and contains synthetic bristles, but its physical construction and characteristics are different from a dental brush or toothbrush. The handle 46 has a curved appearance as seen in FIG. 12 and defines an oblong throughgoing aperture 48 which allows the brush to be hung on a projection. The end 49 of the handle is preferably rounded but can take the respective shapes shown in FIGS. 34–39.

Figure 22:
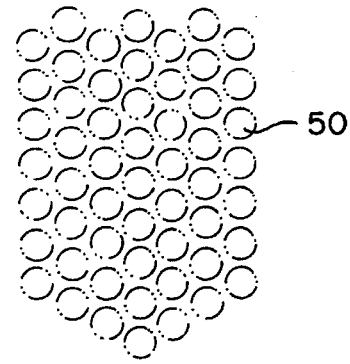
FIG. 22 is a top plan view of an oblique lined bristle assembly used on the head of the lingual brush.
Figure 23:
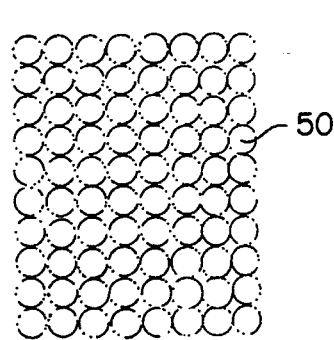
FIG. 23 is a top plan view of an orthogonal lined bristle assembly used on the head of the lingual brush.
Figure 24:
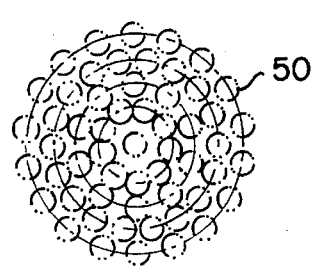
FIG. 24 is a top plan view of a concentric circle bristle assembly used on the head of the lingual brush.
Figure 25:
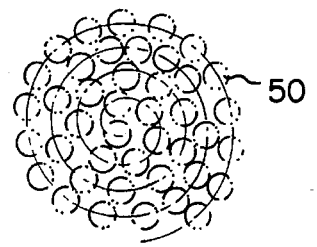
FIG. 25 is a top plan view of a spiral bristle assembly used on the head of the lingual brush.
Figure 26:
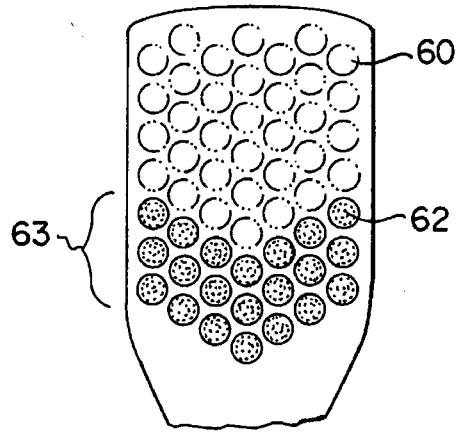
FIG. 26 is a partial top plan view of a rectangular shaped head and varying hardness bristle assembly of the lingual brush.
Figure 27:
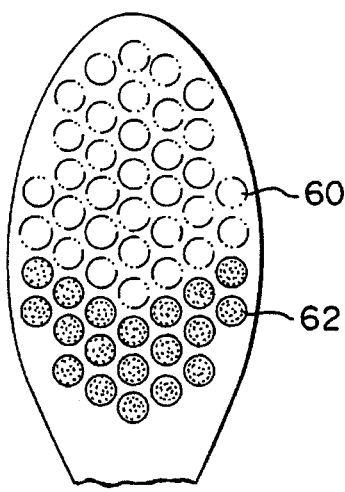
FIG. 27 is a partial top plan view of an oblong shaped head and varying hardness bristle assembly of the lingual brush.
Figure 28:
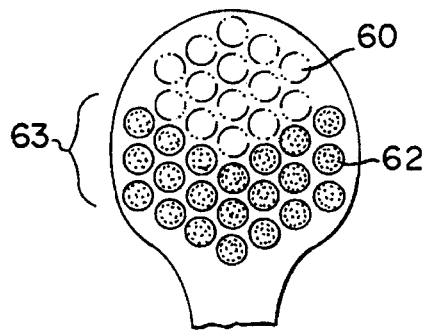
FIG. 28 is a partial top plan view of a rounded shaped head and varying hardness bristle assembly of the lingual brush.
Figure 29:
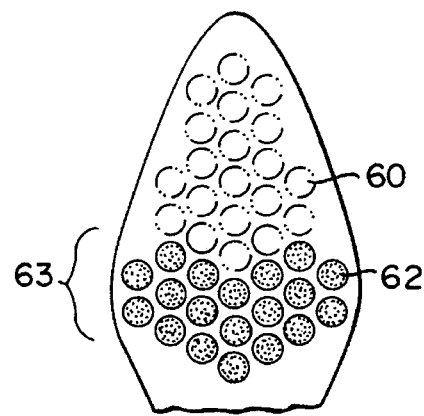
FIG. 29 is a partial top plan view of a blunted triangular shaped head and varying hardness bristle assembly of the lingual brush.
Figure 40:
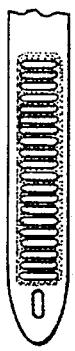
FIG. 40 is a top partial plan view of a rippled handle of the lingual brush.
Figure 30:
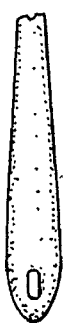
FIG. 30 is a partial top plan view of a rounded teaspoon type handle of the lingual brush.
Figure 31:
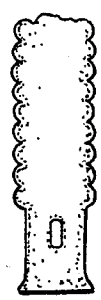
FIG. 31 is a partial top plan view of an undulating or serrated handle of the lingual brush.
Figure 32:
FIG. 32 is a partial top plan view of a rectangular handle of the lingual brush.
Figure 33:
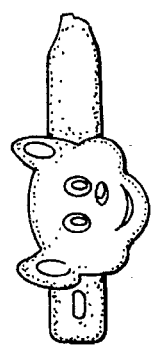
FIG. 33 is a partial top plan view of a rectangular handle such as that shown in FIG. 32 with an applied animal face.
Figure 34:
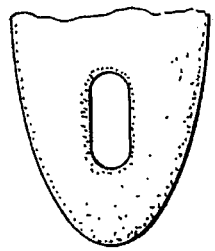
FIG. 34 is an enlarged partial top plan view of a rounded handle end of the lingual brush.
Figure 35:
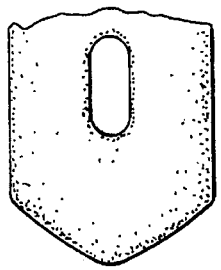
FIG. 35 is an enlarged partial top plan view of a angular handle end of the lingual brush.
Figure 36:
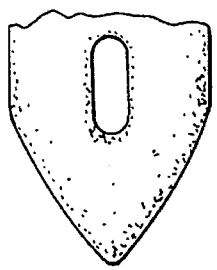
FIG. 36 is an enlarged partial top plan view of a pointed handle end of the lingual brush.
Figure 37:
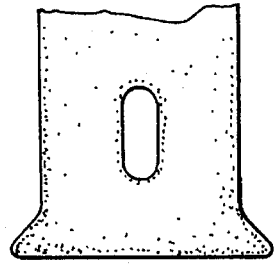
FIG. 37 is an enlarged partial top plan view of a flanged handle end of the lingual brush.
Figure 38:
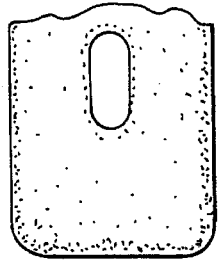
FIG. 38 is an enlarged partial top plan view of a substantially rectangular handle end of the lingual brush.
Figure 39:
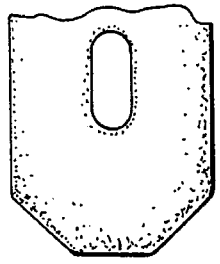
FIG. 39 is an enlarged partial top plan view of a semi octagonal handle end of the lingual brush.

The head 42 is preferably rectangular as shown in plan view in FIG. 26 but can take the alternate shapes shown in FIGS. 27–29. It should be noted that the distal end 43 of the head is not as thick as the proximal end 45 providing a tapered profile allowing easy insertion into the mouth. The head 42 has a flat brush surface provided with an assembly of bristle cells 50 which are imbedded in the body of the head and extend outward from the face 51 at least 5 mm, or in the range of 4–6 mm. The bristle cell distribution on the head is comprised of a series of cells 50, each of which contains approximately 20 synthetic bristles. The cells number anywhere from about 35 to about 65 depending on the head shape. The cells can be arranged in an oblique line configuration as shown in FIG. 22, an orthogonal line configuration as shown in FIG. 23, a concentric circular configuration as shown in FIG. 24, or a spiral configuration as shown in FIG. 25. The outer brush head surface 47 is arcuate or rounded as is seen in FIGS. 11 and 12. As seen in FIGS. 18 through 21, the bristle cells can be provided with flat ends 52, peaked ends 54, round ends 56 and opposing inclined ends 58. Preferably, the synthetic bristle cells 50 are located all in the base with hard synthetic bristle cells 60 being positioned in the superior middle of the base and softer synthetic bristle cells 62 are positioned on the inferior middle of the base forming a V or chevron 63. If desired the synthetic bristle cells can be composed of all hard bristles as is shown in FIG. 16 or of all softer bristle cells.

The preferred embodiment of the invention uses the rectangular head as shown in FIG. 26 with alternative embodiments using the oval or football shaped head as shown in FIG. 27, the round head as shown in FIG. 28, or the rounded triangular head as shown in FIG. 29. The rounded triangular head is specifically designed with fewer bristles in the superior area to get a minimum gag reflex.

The neck angle orientation in regard to the brush head axis is flat in the embodiment shown in FIG. 1 and ranges from 10° to 15° in the embodiments shown in FIGS. 4, 7, 10 and 13.

In the lingual brush embodiment as shown by FIGS. 1 through 3, the head 42 in plan view has a square or rectangular configuration with a length ranging from 2.5 cm to 3.5 cm, and a neck 44 having a length ranging from 3.5 cm to 4.0 cm with a width ranging from 0.8 cm to 1.0 cm. The handle 46 has a length ranging from 9.0 cm to 11.5 cm with a width ranging from 1.5 cm to 2.0 cm. There is no angle between the head and the neck and the device follows a straight line from head to the bottom of the handle. The overall length of the brush depending on whether it is a small, medium or large, ranges between 15 cm and 19 cm.

The embodiment shown in FIGS. 4 through 6 is provided with a rectangular head 42 having a length ranging from 2.5 cm to 3.5 cm with a width ranging from 1.5 cm to 2.5 cm. The neck 44 has a length ranging from 3.5 cm to 4.0 cm with a width ranging from 0.8 cm to 1.0 cm and forms an angle near the head of 15° for large and medium sizes and 10° for the small size. The handle 46 has a length ranging from 9.0 cm to 11.5 cm with a width ranging from 1.5 cm to 2.5 cm. The overall length of the brush depending on whether it is a small, medium or large, ranges between 15 cm and 19 cm.

The lingual brush embodiment shown in FIGS. 7 through 9 has a rectangular head 42 with a length ranging from 2.5 cm to 3.5 cm and a width ranging from 1.5 cm to 2.5 cm. The neck 44 has a length ranging from 3.5 cm to 4.0 cm and a width ranging from 0.8 cm to 1.0 cm. The brush is provided with an angle in the middle of the neck of about 15° for large and medium sizes and 10° for the small size so that the neck forms a partially curved element. The handle 46 ranges from a length from 9.0 cm to 11.5 cm and has a width ranging from 1.5 cm to 2.5 cm. The overall length of the brush ranges from 15 cm to 19 m depending upon the size used.

The embodiment shown in FIGS. 13 through 15 has has a rectangular head 42 with a length ranging from 2.5 cm to 3.5 cm and a width ranging from 1.5 cm to 2.5 cm. It is provided with a neck 44 having a length of 3.5 cm to 4.0 cm and a width of 0.8 cm to 1.0 cm extends from the head, forming an angle close to 15°, with the other end of the neck next to the handle forming an angle of 15° for large and medium sizes and 10° for the small size. It can thus be seen that the brush has two angles, one near the head and the other one near the handle, so that the head and handle are parallel. The handle 46 has a length ranging from 9.0 cm to 11.5 cm and a width ranging from 1.5 cm to 2.5 cm. The brush has a total overall length ranging from 15 cm to 19 cm depending upon the size of the brush.

While each of the embodiments are usable, the embodiment shown by FIGS. 10 through 12 is more comfortable for use in home uses, while the other embodiments are convenient for clinical and hospital uses.

In operation the lingual brush is grasped in either hand by the handle 46 and is inserted into the mouth as one would a conventional toothbrush. The head of the brush with the bristles is moved in a posterior-anterior direction along the dorsal surface of the tongue. The bristle cells 50 loosen and clean debris, food and other materials including bacteria from the grooves, furrows, and papillae of the dorsal surface of the tongue, similar to a toothbrush engaging the teeth. Because of the specific design of the brush 40, the dorsal surface of the tongue will be cleaned efficiently and quickly without triggering a gag reflex. Simple rinsing of the mouth will remove the loosened debris from the oral cavity. The brush is then rinsed off and stored in a conventional manner.

In the foregoing description, the invention has been described with reference to a particular preferred embodiment, although it is to be understood that specific details shown are merely illustrative, and the invention may be carried out in other ways without departing from the true spirit and scope of the following claims.

What is claimed is:

1. A device for cleaning the surface of the tongue, comprising:
   (a) an elongated handle;
   (b) an elongated neck portion having a first end connected to an end of said handle and an opposite second end, said neck portion and said handle cooperating to define an angle ranging from about 10 to 15 degrees;
   (c) an elongated brush head having a proximal end and a distal end, the proximal end of the brush head being connected to the second end of said neck portion, the brush head being thicker at the proximal end thereof and tapering to the distal end thereof to minimize the gag reflex when brushing the back of the tongue, the brush head having a flat surface, rounded sides and a rounded surface opposing said flat surface;
   (d) a plurality of bristle cells fixed to and extending from the flat surface of the brush head, each bristle cell being directed away from the axis of the handle and comprising a plurality of bristles, each bristle having a length in the range of 4 to 6 millimeters; and
   (e) said bristle cells being arranged in a plurality of groups, each group having a different hardness with the bristle cells of each respective group having the same degree of hardness, the groups being arranged along the length of the brush head from the proximal end to the distal end thereof, the group at the proximal end of said brush head and nearest the neck portion being the softest in hardness, said groups being arranged on said brush head in a plurality of v-shaped rows.

2. The device of claim 1 wherein said brush head is ellipsoidal in shape.

3. The device of claim 1 wherein said bristle cells are comprised of bristles of varying length forming bristle cells with a peaked end surface.

4. A lingual brush as claimed in claim 1 wherein said group of bristles proximate to the handle form a chevron shaped pattern.

5. The device of claim 1 wherein said brush head is triangular in shape.

6. The device of claim 1 wherein said brush head is substantially rectangular in shape.

7. The device of claim 1 wherein said bristle cells are comprised of bristles of uniform length forming a flat end surface.

8. The device of claim 1 wherein said bristle cells are comprised of bristles of varying lengths forming inclined end surfaces for each bristle cell.

9. The device of claim 1 wherein said angle is positioned close to the brush head.

10. The device of claim 1 wherein said angle is positioned in the middle of the neck portion.

11. The device of claim 1 wherein said angle is positioned close to the handle.

12. The device of claim 1 wherein said bristle cells are made of synthetic and natural materials.

13. The device of claim 1 wherein said handle is provided on its inner face with ripple means.

* * * * *